United States Patent [19]

Nguyen-Senderowicz

[11] Patent Number: 5,445,598

[45] Date of Patent: Aug. 29, 1995

[54] BRACE FOR INFANT FOOTWEAR, NAMELY, SOCKS, SOFT SHOES, BOOTIES AND/OR MOCCASINS

[76] Inventor: Khôi Nguyen-Senderowicz, Berkeley Main 2000 Allston Way, Berkeley, Calif. 94704

[21] Appl. No.: 79,648

[22] Filed: Jun. 21, 1993

[51] Int. Cl.$^6$ .................................. A61F 5/00
[52] U.S. Cl. ............................. 602/65; 602/28
[58] Field of Search ........ 602/28, 41, 60, 61, 602/65, 66; 482/79, 105

[56] References Cited

U.S. PATENT DOCUMENTS

| | | | |
|---|---|---|---|
| 1,211,055 | 1/1917 | Bernstein | 602/65 |
| 1,441,907 | 1/1923 | Bernstein | 602/65 |
| 3,334,898 | 8/1967 | McCrory et al. | 482/79 X |
| 4,384,717 | 5/1983 | Morris | 273/156 |
| 4,809,974 | 3/1989 | Buhr | 482/105 X |
| 4,817,589 | 4/1989 | Wertz | 602/28 |
| 4,936,571 | 6/1990 | Buhr | 482/105 X |

FOREIGN PATENT DOCUMENTS

| | | | |
|---|---|---|---|
| 8700578 | 10/1988 | Netherlands | 602/65 |
| 427217 | 4/1935 | United Kingdom | 602/65 |

*Primary Examiner*—Linda C. M. Dvorak

[57] ABSTRACT

A brace for keeping the socks, soft shoes, booties and moccasins of infants from falling off when being worn. The brace is comprised of an elastic Möobius band. This band is first slipped over the foot to rest around the ankle portion of the footwear being worn. Once positioned there, it is then twisted once to form another loop which is stretched over the foot and released around the arch portion of the footwear. When properly worn, the brace provides three sources (20,22,24) of counter tension to hold the infant footwear snugly yet comfortably intact. This brace can also be fully incorporated into the soft shoe/moccasin/booty itself by constructing in the applicable footwear a casing (26) to hold the elastic band, which when inserted through the casing will form the brace as well as serve as a shoe lace for adjusting the fit.

2 Claims, 2 Drawing Sheets

BRACE FOR INFANT FOOTWEAR, NAMELY, SOCKS, SOFT SHOES, BOOTIES AND/OR MOCCASINS

BACKGROUND—FIELD OF INVENTION

This invention relates to socks, soft shoes, booties and/or moccasins for infants, specifically a device for holding said footwear intact while being worn.

BACKGROUND—DESCRIPTION OF PRIOR ART

It has always been a problem with infants to keep their socks and shoes from falling off, whether because of their tendency to pull off the said items or through normal usage. Such is the case that many types of clothing/footwear have been created which have attempted to address this problem. These range from footed pants to booties and/or moccasins with tie straps/laces. While the footed pants work to keep the feet covered, they are limited in that they must be used as an entire piece, i.e., there is no option of separating the pants from the foot covers, etc.

Booties and moccasins, such as "T.V. booties" have been created to serve as comfortable, practical alternatives to regular "hard" shoes, which for infants can be quite inconvenient to put on, and more importantly, uncomfortable and constricting to wear. While these soft shoes provide laces or straps for tying, they nevertheless suffer from the problem of slipping off quite easily, and moreover, infants can and do easily pull on the laces and shoes to eventually remove them. Thus soft shoes such as booties tend to fall off easily, unless of course one were to overtighten the laces and thereby render them extremely uncomfortable if not dangerous (restricting circulation, etc.) to wear.

Socks have also been modified for infants in an effort to prevent their slipping off. Normally, these modifications consist of either: (1) the use of a highly elastic fabric throughout the sock, such as nylon or cotton with an inner core made out of rubber fibres, or (2) the use of an elastic band constructed into the cuff of the sock. Some of the problems associated with option (1) is that neither of the materials permit adequate ventilation and their texture is not as comfortable as a fabric with a high content of pure cotton. The problem with option (2) is that in order to achieve any efficiency the band has to exercise a high degree of tension, thus constricting the blood circulation, as can be seen from the resulting impression marks left on the skin. In any case, neither option (1) nor (2) manages to prevent nor discourage the determined/bored infant from successfully pulling off his/her socks.

Thus heretofore no real workable solution has been devised to prevent the "accidental" slipping off and/or subsequent loss of infant socks, soft shoes, booties and/or moccasins.

OBJECTS AND ADVANTAGES

Accordingly, several objects and advantages of this invention are:

(a) to provide a brace for infant socks, soft shoes, booties and/or moccasins that is so functional and versatile that it can be used in conjunction with any of the above to keep them intact;

(b) to provide a footwear brace which is safe to use;

(c) to provide a footwear brace which is comfortable to wear;

(d) to provide a footwear brace which is extremely easy and convenient to use;

(e) to provide a footwear brace whose production is extremely convenient, rapid, and economical;

(f) to provide a footwear brace that is so simple and unobtrusive that as an accessory it does not detract from the aesthetic quality of the footwear with which it is being used.

Further objects and advantages will become apparent from a consideration of the ensuing description and drawings.

DRAWINGS FIGURES

REFERENCE NUMERALS IN DRAWINGS

Figure 1:
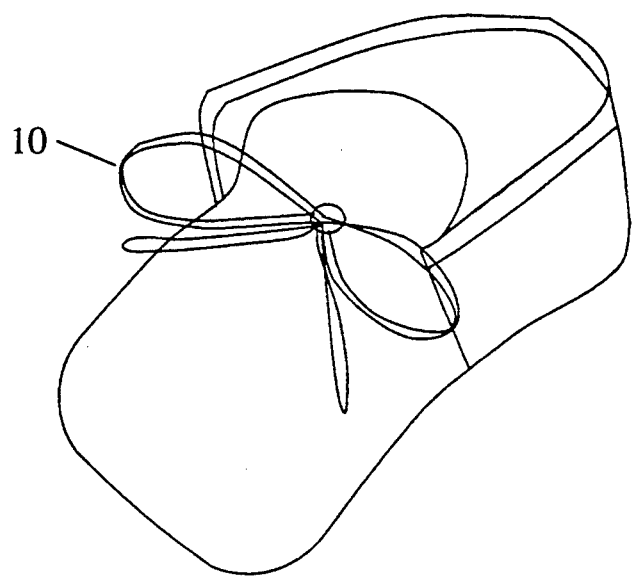
FIG. 1 shows a typical booty/moccasin.

10: lace around ankle
12: twist of Möbius band
14: seam where ends are sewn together
16: co-linear components with the elastic
18: applied force
20: crisscross in center front
22: loop around ankle
24: loop around arch
26 casing in shoe for brace
28: rear outlet for elastic lace

DESCRIPTION—FIGS. 1 TO 5

Figure 2:
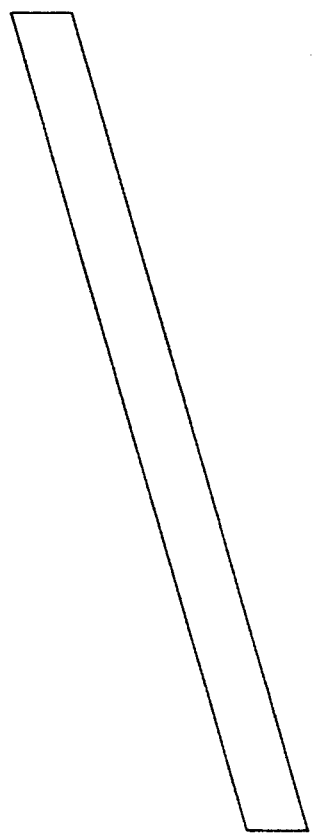
FIG. 2 shows a strip of elastic used to make the retaining band.
Figure 3:
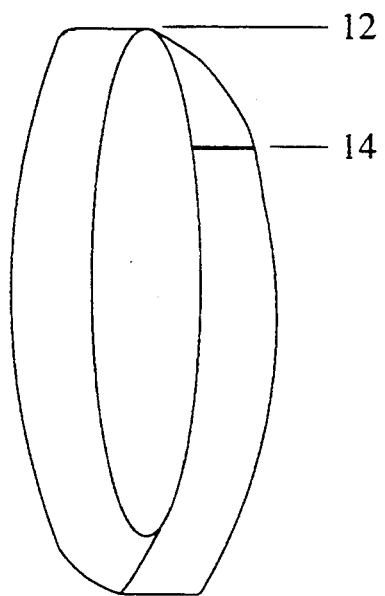
FIG. 3 shows the strip of elastic sewn together to form a Möbius band.
Figure 6:
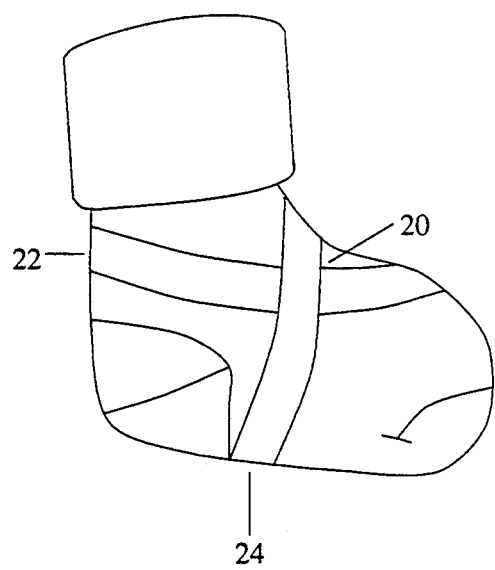
FIG. 6 shows a side view of the brace properly worn over a sock.

The solution proposed in this application is based on the simple idea of taking an endless loop of elastic and wrapping it around the ankle and the arch of the foot, according to FIG. 6. The construction of a typical embodiment of the bracing device of this invention is illustrated in FIGS. 2 and 3. In the preferred embodiment, a piece of braided, shrink resistant (69% polyester, 31% rubber) elastic is used (FIG. 2). The dimensions of this strip of elastic are roughly ten inches long by half an inch wide so that when worn the fit is snug yet comfortable.

In order to achieve maximum comfort, the band formed should lie as flat as possible. A simple cylindrical band would present a problem when a double loop is made. The region of the band inside the circle would have a bend. This protuberance is a potential element of discomfort. So the remaining problem is to find a topology such that there is no need for this bend. A Möbius surface, sometimes also referred to as a single surface shape, attains the loops without the need for sharp bends. Thus, as shown in FIG. 3, the piece of elastic is twisted once (12) and sewn together at the ends (14) to form an elastic Möbius band. This band, when twisted to form the second loop (FIG. 4), yields a brace which is flat and smooth to wear (FIG. 6).

OPERATION—FIGS. 3 to 6

Figure 4:
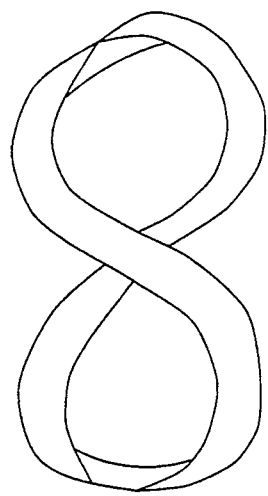
FIG. 4 shows the looped "8" form that the band will take once it is worn.
Figure 5:
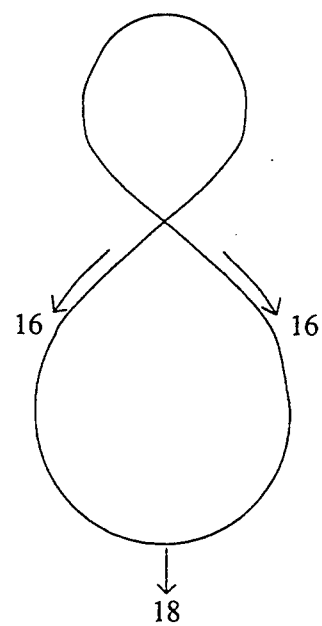
FIG. 5 shows the stretching and tightening effect between the two loops.

The manner of using the bracing device of this invention is quite simple. FIGS. 4 through 6 illustrate how the elastic band is used to hold a sock in place over a foot. The method for bracing any other footwear would be identical. The band of FIG. 3 is first slipped over the foot to rest around the ankle portion of the sock. FIG. 4 shows how the band is then twisted from the front side to form a figure "8" and therefore another loop. This remaining free loop is then slipped over the foot to rest around the arch portion of the foot itself. FIG. 6 shows a side view of the band once it is fully inserted. When properly worn the band is crisscrossed (20) in the center front of the ankle.

For a better understanding of the functioning of this brace, FIG. 5 shows the band by itself and the vectorial components of the force that is applied to the loop encircling the bottom of the foot in the downward direction, indicated by 18. This force is decomposed in 16 which increases the tension around the ankle, thus impeding the slippage of the footwear underneath. This incremental tension is just temporary, unlike in the case where there is only one band around the ankle. Note that whereas socks, moccasins and booties have only one source of constant "binding retention" (FIG. 1, 10), i.e., around the ankle, the retention band of this invention automatically provides three optimum sources: one loop (22) around the ankle, another counter balancing one (24) around the foot itself, and a crisscross reinforcement section (20) across the front. All this is provided without sacrificing comfort. In fact, the use of flexible elastic in itself, rather than the conventional shoe laces made of string, ribbon, etc., provides for ideal comfort and holding power. Such is the case that for its comfort and retention qualifies, elastic has always been the preferred material for use in underwear, sleeve ends, etc.

Tried and tested on the most active of babies under various circumstances, the device of this invention has withstood the most rigorous of tests. For example, seated alone (undistracted by others) in her car seat with nothing but her foot coverings to amuse herself, baby has managed to easily remove all of the "control" items, i.e., sock, moccasin, and shoe, but not the sock with the elastic brace. These remained intact, even when they presented the only source of "temptation/mischief". The snugly fitting form combined with the thin elastic material of the device make it very difficult for baby fingers to "pick at" and remove. Most importantly, although baby is unable to remove the elastic band, she does not seem to be at all discomforted by it either.

SUMMARY, RAMIFICATIONS, AND SCOPE

Accordingly, the reader will see that while extremely easy and convenient to use and produce, the retaining device of this invention is perfectly suited to the purpose of comfortably yet effectively holding intact the socks, soft shoes, moccasins and booties of infants, a problem that heretofore has not been successfully solved.

Figure 7:
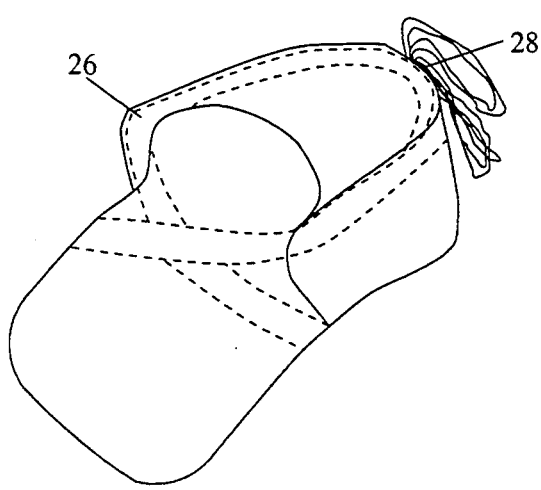
FIG. 7 shows a side view of how the brace can be constructed into the shoe itself.

Although the above description contains many specificities, these should not be construed as limiting the scope of the invention but as merely providing illustrations of some of the presently preferred embodiments of this invention. For example, the device need not necessarily be used as a separate accessory, but also can be constructed and fully incorporated into the shoe, moccasin or booty itself (FIG. 7). In other words, instead of the traditional shoe lace with casing around the ankle, a casing (26) conforming to the "8" configuration of the design of this invention can be implemented and an elastic type shoe lace drawn through that. This elastic shoe lace can be made to tie (for adjusting the fit) either at the center front or rear of the ankle (28), depending on where the casing holes are designed to meet. Alternatively, the sock can be modified to have a more durable sole (e.g., leather, etc.) to serve as an all-in-one sock/soft shoe to be used in conjunction with the brace.

Thus the scope of the invention should be determined by the appended claims and their legal equivalents, rather than by the examples given.

I claim:

1. An infant footwear brace in combination with infant footwear, said brace used to keep said footwear intact when being worn, said brace comprising:
    (a) a single endless flat narrow strap of elastic formed in a Möbius band and with said strap having a width of about half an inch and a length greater than about 8 inches and less than about 24 inches,
    (b) said strap having a first portion wrapping in a flat untwisted manner around the ankle portion of said footwear,
    (c) said strap having a second portion wrapping in a flat untwisted manner around the arch portion of said footwear, each of said first and second portions merging to crisscross centrally at the front of the ankle portion of said footwear.

2. The infant footwear brace of claim 1 wherein the ends of said strap are sewn together.

* * * * *